(12) United States Patent
Kulkarni et al.

(10) Patent No.: US 9,170,211 B2
(45) Date of Patent: Oct. 27, 2015

(54) DESIGN-BASED INSPECTION USING REPEATING STRUCTURES

(75) Inventors: Ashok V. Kulkarni, San Jose, CA (US); Chien-Huei (Adam) Chen, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 776 days.

(21) Appl. No.: 13/420,224

(22) Filed: Mar. 14, 2012

(65) Prior Publication Data

US 2012/0243773 A1    Sep. 27, 2012

Related U.S. Application Data

(60) Provisional application No. 61/467,964, filed on Mar. 25, 2011.

(51) Int. Cl.
| | | |
|---|---|---|
| *G06K 9/00* | (2006.01) | |
| *G01N 21/956* | (2006.01) | |
| *G01N 21/95* | (2006.01) | |

(52) U.S. Cl.
CPC ...... *G01N 21/95607* (2013.01); *G01N 21/9501* (2013.01)

(58) Field of Classification Search
None
See application file for complete search history.

(56) References Cited

U.S. PATENT DOCUMENTS

| | | |
|---|---|---|
| 3,495,269 A | 2/1970 | Mutschler et al. |
| 3,496,352 A | 2/1970 | Jugle |
| 3,909,602 A | 9/1975 | Micka |
| 4,015,203 A | 3/1977 | Verkuil |
| 4,247,203 A | 1/1981 | Levy et al. |
| 4,347,001 A | 8/1982 | Levy et al. |
| 4,378,159 A | 3/1983 | Galbraith |
| 4,448,532 A | 5/1984 | Joseph et al. |
| 4,475,122 A | 10/1984 | Green |
| 4,532,650 A | 7/1985 | Wihl et al. |
| 4,555,798 A | 11/1985 | Broadbent, Jr. et al. |
| 4,578,810 A | 3/1986 | MacFarlane et al. |
| 4,579,455 A | 4/1986 | Levy et al. |
| 4,595,289 A | 6/1986 | Feldman et al. |
| 4,599,558 A | 7/1986 | Castellano, Jr. et al. |
| 4,633,504 A | 12/1986 | Wihl |
| 4,641,353 A | 2/1987 | Kobayashi |
| 4,641,967 A | 2/1987 | Pecen |
| 4,734,721 A | 3/1988 | Boyer et al. |
| 4,748,327 A | 5/1988 | Shinozaki et al. |
| 4,758,094 A | 7/1988 | Wihl et al. |

(Continued)

FOREIGN PATENT DOCUMENTS

| | | |
|---|---|---|
| CN | 1339140 | 3/2002 |
| CN | 1398348 | 2/2003 |

(Continued)

OTHER PUBLICATIONS

Phan et al., "Comparison of Binary Mask Defect Printability Analysis Using Virtual Stepper System and Aerial Image Microscope System," Proceedings of SPIE—The International Society for Optical Engineering 1999 Society of Photo-Optical Instrumentation Engineers, vol. 3873, 1999, pp. 681-692.

(Continued)

*Primary Examiner* — Sumati Lefkowitz
*Assistant Examiner* — David Perlman
(74) *Attorney, Agent, or Firm* — Ann Marie Mewherter (57) ABSTRACT

Systems and methods for design-based inspection using repeating structures are provided.

35 Claims, 4 Drawing Sheets

(56) References Cited

U.S. PATENT DOCUMENTS

| | | |
|---|---|---|
| 4,766,324 A | 8/1988 | Saadat et al. |
| 4,799,175 A | 1/1989 | Sano et al. |
| 4,805,123 A | 2/1989 | Specht et al. |
| 4,812,756 A | 3/1989 | Curtis et al. |
| 4,814,829 A | 3/1989 | Kosugi et al. |
| 4,817,123 A | 3/1989 | Sones et al. |
| 4,845,558 A | 7/1989 | Tsai et al. |
| 4,877,326 A | 10/1989 | Chadwick et al. |
| 4,926,489 A | 5/1990 | Danielson et al. |
| 4,928,313 A | 5/1990 | Leonard et al. |
| 5,046,109 A | 9/1991 | Fujimori et al. |
| 5,124,927 A | 6/1992 | Hopewell et al. |
| 5,189,481 A | 2/1993 | Jann et al. |
| 5,355,212 A | 10/1994 | Wells et al. |
| 5,444,480 A | 8/1995 | Sumita |
| 5,453,844 A | 9/1995 | George et al. |
| 5,481,624 A | 1/1996 | Kamon |
| 5,485,091 A | 1/1996 | Verkuil |
| 5,497,381 A | 3/1996 | O'Donoghue et al. |
| 5,528,153 A | 6/1996 | Taylor et al. |
| 5,544,256 A | 8/1996 | Brecher et al. |
| 5,563,702 A | 10/1996 | Emery et al. |
| 5,572,598 A | 11/1996 | Wihl et al. |
| 5,578,821 A | 11/1996 | Meisberger et al. |
| 5,594,247 A | 1/1997 | Verkuil et al. |
| 5,608,538 A | 3/1997 | Edgar et al. |
| 5,619,548 A | 4/1997 | Koppel |
| 5,621,519 A | 4/1997 | Frost et al. |
| 5,644,223 A | 7/1997 | Verkuil |
| 5,650,731 A | 7/1997 | Fung et al. |
| 5,661,408 A | 8/1997 | Kamieniecki et al. |
| 5,689,614 A | 11/1997 | Gronet et al. |
| 5,694,478 A | 12/1997 | Braier et al. |
| 5,696,835 A | 12/1997 | Hennessey et al. |
| 5,703,969 A | 12/1997 | Hennessey et al. |
| 5,716,889 A | 2/1998 | Tsuji et al. |
| 5,737,072 A | 4/1998 | Emery et al. |
| 5,742,658 A | 4/1998 | Tiffin et al. |
| 5,754,678 A | 5/1998 | Hawthorne et al. |
| 5,767,691 A | 6/1998 | Verkuil |
| 5,767,693 A | 6/1998 | Verkuil |
| 5,771,317 A | 6/1998 | Edgar |
| 5,773,989 A | 6/1998 | Edelman et al. |
| 5,774,179 A | 6/1998 | Chevrette et al. |
| 5,795,685 A | 8/1998 | Liebmann et al. |
| 5,822,218 A | 10/1998 | Moosa et al. |
| 5,831,865 A | 11/1998 | Berezin et al. |
| 5,834,941 A | 11/1998 | Verkuil |
| 5,852,232 A | 12/1998 | Samsavar et al. |
| 5,866,806 A | 2/1999 | Samsavar et al. |
| 5,874,733 A | 2/1999 | Silver et al. |
| 5,884,242 A | 3/1999 | Meier et al. |
| 5,889,593 A | 3/1999 | Bareket |
| 5,917,332 A | 6/1999 | Chen et al. |
| 5,932,377 A | 8/1999 | Ferguson et al. |
| 5,940,458 A | 8/1999 | Suk |
| 5,948,972 A | 9/1999 | Samsavar et al. |
| 5,955,661 A | 9/1999 | Samsavar et al. |
| 5,965,306 A | 10/1999 | Mansfield et al. |
| 5,978,501 A | 11/1999 | Badger et al. |
| 5,980,187 A | 11/1999 | Verhovsky |
| 5,986,263 A | 11/1999 | Hiroi et al. |
| 5,991,699 A | 11/1999 | Kulkarni et al. |
| 5,999,003 A | 12/1999 | Steffan et al. |
| 6,011,404 A | 1/2000 | Ma et al. |
| 6,014,461 A | 1/2000 | Hennessey et al. |
| 6,040,911 A | 3/2000 | Nozaki et al. |
| 6,040,912 A | 3/2000 | Zika et al. |
| 6,052,478 A | 4/2000 | Wihl et al. |
| 6,060,709 A | 5/2000 | Verkuil et al. |
| 6,072,320 A | 6/2000 | Verkuil |
| 6,076,465 A | 6/2000 | Vacca et al. |
| 6,078,738 A | 6/2000 | Garza et al. |
| 6,091,257 A | 7/2000 | Verkuil et al. |
| 6,091,846 A | 7/2000 | Lin et al. |
| 6,097,196 A | 8/2000 | Verkuil et al. |
| 6,097,887 A | 8/2000 | Hardikar et al. |
| 6,104,206 A | 8/2000 | Verkuil |
| 6,104,835 A | 8/2000 | Han |
| 6,117,598 A | 9/2000 | Imai |
| 6,121,783 A | 9/2000 | Horner et al. |
| 6,122,017 A | 9/2000 | Taubman |
| 6,122,046 A | 9/2000 | Almogy |
| 6,137,570 A | 10/2000 | Chuang et al. |
| 6,141,038 A | 10/2000 | Young et al. |
| 6,146,627 A | 11/2000 | Muller et al. |
| 6,171,737 B1 | 1/2001 | Phan et al. |
| 6,175,645 B1 | 1/2001 | Elyasaf et al. |
| 6,184,929 B1 | 2/2001 | Noda et al. |
| 6,184,976 B1 | 2/2001 | Park et al. |
| 6,191,605 B1 | 2/2001 | Miller et al. |
| 6,201,999 B1 | 3/2001 | Jevtic |
| 6,202,029 B1 | 3/2001 | Verkuil et al. |
| 6,205,239 B1 | 3/2001 | Lin et al. |
| 6,215,551 B1 | 4/2001 | Nikoonahad et al. |
| 6,224,638 B1 | 5/2001 | Jevtic et al. |
| 6,233,719 B1 | 5/2001 | Hardikar et al. |
| 6,246,787 B1 | 6/2001 | Hennessey et al. |
| 6,248,485 B1 | 6/2001 | Cuthbert |
| 6,248,486 B1 | 6/2001 | Dirksen et al. |
| 6,259,960 B1 | 7/2001 | Inokuchi |
| 6,266,437 B1 | 7/2001 | Eichel et al. |
| 6,267,005 B1 | 7/2001 | Samsavar et al. |
| 6,268,093 B1 | 7/2001 | Kenan et al. |
| 6,272,236 B1 | 8/2001 | Pierrat et al. |
| 6,282,309 B1 | 8/2001 | Emery |
| 6,292,582 B1 | 9/2001 | Lin et al. |
| 6,295,374 B1 | 9/2001 | Robinson et al. |
| 6,324,298 B1 | 11/2001 | O'Dell et al. |
| 6,344,640 B1 | 2/2002 | Rhoads |
| 6,363,166 B1 | 3/2002 | Wihl et al. |
| 6,366,687 B1 | 4/2002 | Aloni et al. |
| 6,373,975 B1 | 4/2002 | Bula et al. |
| 6,388,747 B2 | 5/2002 | Nara et al. |
| 6,393,602 B1 | 5/2002 | Atchison et al. |
| 6,407,373 B1 | 6/2002 | Dotan |
| 6,415,421 B2 | 7/2002 | Anderson et al. |
| 6,445,199 B1 | 9/2002 | Satya et al. |
| 6,451,690 B1 | 9/2002 | Matsumoto et al. |
| 6,459,520 B1 | 10/2002 | Takayama |
| 6,466,314 B1 | 10/2002 | Lehman |
| 6,466,315 B1 | 10/2002 | Karpol et al. |
| 6,470,489 B1 | 10/2002 | Chang et al. |
| 6,483,938 B1 | 11/2002 | Hennessey et al. |
| 6,513,151 B1 | 1/2003 | Erhardt et al. |
| 6,526,164 B1 | 2/2003 | Mansfield et al. |
| 6,529,621 B1 | 3/2003 | Glasser et al. |
| 6,535,628 B2 | 3/2003 | Smargiassi et al. |
| 6,539,106 B1 | 3/2003 | Gallarda et al. |
| 6,569,691 B1 | 5/2003 | Jastrzebski et al. |
| 6,581,193 B1 | 6/2003 | McGhee et al. |
| 6,593,748 B1 | 7/2003 | Halliyal et al. |
| 6,597,193 B2 | 7/2003 | Lagowski et al. |
| 6,602,728 B1 | 8/2003 | Liebmann et al. |
| 6,608,681 B2 | 8/2003 | Tanaka et al. |
| 6,614,520 B1 | 9/2003 | Bareket et al. |
| 6,631,511 B2 | 10/2003 | Haffner et al. |
| 6,636,301 B1 | 10/2003 | Kvamme et al. |
| 6,642,066 B1 | 11/2003 | Halliyal et al. |
| 6,658,640 B2 | 12/2003 | Weed |
| 6,665,065 B1 | 12/2003 | Phan et al. |
| 6,670,082 B2 | 12/2003 | Liu et al. |
| 6,680,621 B2 | 1/2004 | Savtchouk |
| 6,691,052 B1 | 2/2004 | Maurer |
| 6,701,004 B1 | 3/2004 | Shykind et al. |
| 6,718,526 B1 | 4/2004 | Eldredge et al. |
| 6,721,695 B1 | 4/2004 | Chen et al. |
| 6,734,696 B2 | 5/2004 | Horner et al. |
| 6,738,954 B1 | 5/2004 | Allen et al. |
| 6,748,103 B2 | 6/2004 | Glasser et al. |
| 6,751,519 B1 | 6/2004 | Satya et al. |
| 6,753,954 B2 | 6/2004 | Chen |
| 6,757,645 B2 | 6/2004 | Chang et al. |
| 6,759,655 B2 | 7/2004 | Nara et al. |

(56) References Cited

U.S. PATENT DOCUMENTS

| | | |
|---|---|---|
| 6,771,806 B1 | 8/2004 | Satya et al. |
| 6,775,818 B2 | 8/2004 | Taravade et al. |
| 6,777,147 B1 | 8/2004 | Fonseca et al. |
| 6,777,676 B1 | 8/2004 | Wang et al. |
| 6,778,695 B1 | 8/2004 | Schellenberg et al. |
| 6,779,159 B2 | 8/2004 | Yokoyama et al. |
| 6,784,446 B1 | 8/2004 | Phan et al. |
| 6,788,400 B2 | 9/2004 | Chen |
| 6,789,032 B2 | 9/2004 | Barbour et al. |
| 6,803,554 B2 | 10/2004 | Ye et al. |
| 6,806,456 B1 | 10/2004 | Ye et al. |
| 6,807,503 B2 | 10/2004 | Ye et al. |
| 6,813,572 B2 | 11/2004 | Satya et al. |
| 6,820,028 B2 | 11/2004 | Ye et al. |
| 6,828,542 B2 | 12/2004 | Ye et al. |
| 6,842,225 B1 | 1/2005 | Irie |
| 6,859,746 B1 | 2/2005 | Stirton |
| 6,879,403 B2 | 4/2005 | Freifeld |
| 6,879,924 B2 | 4/2005 | Ye et al. |
| 6,882,745 B2 | 4/2005 | Brankner et al. |
| 6,884,984 B2 | 4/2005 | Ye et al. |
| 6,886,153 B1 | 4/2005 | Bevis |
| 6,892,156 B2 | 5/2005 | Ye et al. |
| 6,902,855 B2 | 6/2005 | Peterson et al. |
| 6,906,305 B2 | 6/2005 | Pease et al. |
| 6,918,101 B1 | 7/2005 | Satya et al. |
| 6,919,957 B2 | 7/2005 | Nikoonahad et al. |
| 6,937,753 B1 | 8/2005 | O'Dell et al. |
| 6,948,141 B1 | 9/2005 | Satya et al. |
| 6,959,255 B2 | 10/2005 | Ye et al. |
| 6,966,047 B1 | 11/2005 | Glasser |
| 6,969,837 B2 | 11/2005 | Ye et al. |
| 6,969,864 B2 | 11/2005 | Ye et al. |
| 6,983,060 B1 | 1/2006 | Martinent-Catalot et al. |
| 6,988,045 B2 | 1/2006 | Purdy |
| 6,990,385 B1 | 1/2006 | Smith et al. |
| 7,003,755 B2 | 2/2006 | Pang et al. |
| 7,003,758 B2 | 2/2006 | Ye et al. |
| 7,012,438 B1 | 3/2006 | Miller et al. |
| 7,026,615 B2 | 4/2006 | Takane et al. |
| 7,027,143 B1 | 4/2006 | Stokowski et al. |
| 7,030,966 B2 | 4/2006 | Hansen |
| 7,030,997 B2 | 4/2006 | Neureuther et al. |
| 7,053,355 B2 | 5/2006 | Ye et al. |
| 7,061,625 B1 | 6/2006 | Hwang et al. |
| 7,071,833 B2 | 7/2006 | Nagano et al. |
| 7,103,484 B1 | 9/2006 | Shi et al. |
| 7,106,895 B1 | 9/2006 | Goldberg et al. |
| 7,107,517 B1 | 9/2006 | Suzuki et al. |
| 7,107,571 B2 | 9/2006 | Chang et al. |
| 7,111,277 B2 | 9/2006 | Ye et al. |
| 7,114,143 B2 | 9/2006 | Hanson et al. |
| 7,114,145 B2 | 9/2006 | Ye et al. |
| 7,117,477 B2 | 10/2006 | Ye et al. |
| 7,117,478 B2 | 10/2006 | Ye et al. |
| 7,120,285 B1 | 10/2006 | Spence |
| 7,120,895 B2 | 10/2006 | Ye et al. |
| 7,123,356 B1 | 10/2006 | Stokowski et al. |
| 7,124,386 B2 | 10/2006 | Smith et al. |
| 7,133,548 B2 | 11/2006 | Kenan et al. |
| 7,135,344 B2 | 11/2006 | Nehmadi et al. |
| 7,136,143 B2 | 11/2006 | Smith |
| 7,152,215 B2 | 12/2006 | Smith et al. |
| 7,162,071 B2 | 1/2007 | Hung et al. |
| 7,170,593 B2 | 1/2007 | Honda et al. |
| 7,171,334 B2 | 1/2007 | Gassner |
| 7,174,520 B2 | 2/2007 | White et al. |
| 7,194,709 B2 | 3/2007 | Brankner |
| 7,207,017 B1 | 4/2007 | Tabery et al. |
| 7,231,628 B2 | 6/2007 | Pack et al. |
| 7,236,847 B2 | 6/2007 | Marella |
| 7,271,891 B1 | 9/2007 | Xiong et al. |
| 7,379,175 B1 | 5/2008 | Stokowski et al. |
| 7,383,156 B2 | 6/2008 | Matsusita et al. |
| 7,386,839 B1 | 6/2008 | Golender et al. |
| 7,388,979 B2 | 6/2008 | Sakai et al. |
| 7,418,124 B2 | 8/2008 | Peterson et al. |
| 7,424,145 B2 | 9/2008 | Horie et al. |
| 7,440,093 B1 | 10/2008 | Xiong et al. |
| 7,570,796 B2 | 8/2009 | Zafar et al. |
| 7,676,077 B2 | 3/2010 | Kulkarni et al. |
| 7,683,319 B2 | 3/2010 | Makino et al. |
| 7,738,093 B2 | 6/2010 | Alles et al. |
| 7,739,064 B1 | 6/2010 | Ryker et al. |
| 7,752,584 B2 | 7/2010 | Yang |
| 7,760,929 B2 | 7/2010 | Orbon et al. |
| 7,774,153 B1 | 8/2010 | Smith |
| 7,877,722 B2 | 1/2011 | Duffy et al. |
| 7,890,917 B1 | 2/2011 | Young et al. |
| 7,904,845 B2 | 3/2011 | Fouquet et al. |
| 7,968,859 B2 | 6/2011 | Young et al. |
| 8,073,240 B2 | 12/2011 | Fischer et al. |
| 8,112,241 B2 | 2/2012 | Xiong |
| 8,126,255 B2 | 2/2012 | Bhaskar et al. |
| 2001/0017694 A1 | 8/2001 | Oomori et al. |
| 2001/0019625 A1 | 9/2001 | Kenan et al. |
| 2001/0022858 A1 | 9/2001 | Komiya et al. |
| 2001/0043735 A1 | 11/2001 | Smargiassi et al. |
| 2002/0010560 A1 | 1/2002 | Balachandran |
| 2002/0019729 A1 | 2/2002 | Chang et al. |
| 2002/0026626 A1 | 2/2002 | Randall et al. |
| 2002/0033449 A1 | 3/2002 | Nakasuji et al. |
| 2002/0035461 A1 | 3/2002 | Chang et al. |
| 2002/0035641 A1 | 3/2002 | Kurose et al. |
| 2002/0035717 A1 | 3/2002 | Matsuoka |
| 2002/0054291 A1 | 5/2002 | Tsai et al. |
| 2002/0088951 A1 | 7/2002 | Chen |
| 2002/0090746 A1 | 7/2002 | Xu et al. |
| 2002/0134936 A1 | 9/2002 | Matsui et al. |
| 2002/0144230 A1 | 10/2002 | Rittman |
| 2002/0145734 A1 | 10/2002 | Watkins et al. |
| 2002/0164065 A1 | 11/2002 | Cai et al. |
| 2002/0168099 A1 | 11/2002 | Noy |
| 2002/0176096 A1 | 11/2002 | Sentoku et al. |
| 2002/0181756 A1 | 12/2002 | Shibuya et al. |
| 2002/0186878 A1 | 12/2002 | Hoon et al. |
| 2002/0192578 A1 | 12/2002 | Tanaka et al. |
| 2003/0004699 A1 | 1/2003 | Choi et al. |
| 2003/0014146 A1 | 1/2003 | Fujii et al. |
| 2003/0017664 A1 | 1/2003 | Pnueli et al. |
| 2003/0022401 A1 | 1/2003 | Hamamatsu et al. |
| 2003/0033046 A1 | 2/2003 | Yoshitake et al. |
| 2003/0048458 A1 | 3/2003 | Mieher et al. |
| 2003/0048939 A1 | 3/2003 | Lehman |
| 2003/0057971 A1 | 3/2003 | Nishiyama et al. |
| 2003/0076989 A1 | 4/2003 | Maayah et al. |
| 2003/0086081 A1 | 5/2003 | Lehman |
| 2003/0094572 A1 | 5/2003 | Matsui et al. |
| 2003/0098805 A1 | 5/2003 | Bizjak et al. |
| 2003/0128870 A1 | 7/2003 | Pease et al. |
| 2003/0138138 A1 | 7/2003 | Vacca et al. |
| 2003/0138978 A1 | 7/2003 | Tanaka et al. |
| 2003/0169916 A1 | 9/2003 | Hayashi et al. |
| 2003/0173516 A1 | 9/2003 | Takane et al. |
| 2003/0192015 A1 | 10/2003 | Liu |
| 2003/0207475 A1 | 11/2003 | Nakasuji et al. |
| 2003/0223639 A1 | 12/2003 | Shlain et al. |
| 2003/0226951 A1 | 12/2003 | Ye et al. |
| 2003/0227620 A1 | 12/2003 | Yokoyama et al. |
| 2003/0228050 A1* | 12/2003 | Geshel et al. ............... 382/149 |
| 2003/0228714 A1 | 12/2003 | Smith et al. |
| 2003/0229410 A1 | 12/2003 | Smith et al. |
| 2003/0229412 A1 | 12/2003 | White et al. |
| 2003/0229868 A1 | 12/2003 | White et al. |
| 2003/0229875 A1 | 12/2003 | Smith et al. |
| 2003/0229880 A1 | 12/2003 | White et al. |
| 2003/0229881 A1 | 12/2003 | White et al. |
| 2003/0237064 A1 | 12/2003 | White et al. |
| 2004/0030430 A1 | 2/2004 | Matsuoka |
| 2004/0032908 A1 | 2/2004 | Hagai et al. |
| 2004/0049722 A1 | 3/2004 | Matsushita |
| 2004/0052411 A1 | 3/2004 | Qian et al. |
| 2004/0057611 A1 | 3/2004 | Lee et al. |
| 2004/0066506 A1 | 4/2004 | Elichai et al. |

(56) References Cited

U.S. PATENT DOCUMENTS

| | | |
|---|---|---|
| 2004/0091142 A1 | 5/2004 | Peterson et al. |
| 2004/0094762 A1 | 5/2004 | Hess et al. |
| 2004/0098216 A1 | 5/2004 | Ye et al. |
| 2004/0102934 A1 | 5/2004 | Chang |
| 2004/0107412 A1 | 6/2004 | Pack et al. |
| 2004/0119036 A1 | 6/2004 | Ye et al. |
| 2004/0120569 A1 | 6/2004 | Hung et al. |
| 2004/0133369 A1 | 7/2004 | Pack et al. |
| 2004/0147121 A1 | 7/2004 | Nakagaki et al. |
| 2004/0174506 A1 | 9/2004 | Smith |
| 2004/0179738 A1 | 9/2004 | Dai et al. |
| 2004/0199885 A1 | 10/2004 | Lu et al. |
| 2004/0223639 A1 | 11/2004 | Sato et al. |
| 2004/0228515 A1 | 11/2004 | Okabe et al. |
| 2004/0234120 A1 | 11/2004 | Honda et al. |
| 2004/0243320 A1 | 12/2004 | Chang et al. |
| 2004/0246476 A1 | 12/2004 | Bevis et al. |
| 2004/0254752 A1 | 12/2004 | Wisniewski et al. |
| 2005/0004774 A1 | 1/2005 | Volk et al. |
| 2005/0008218 A1 | 1/2005 | O'Dell et al. |
| 2005/0010890 A1 | 1/2005 | Nehmadi et al. |
| 2005/0013474 A1 | 1/2005 | Sim |
| 2005/0062962 A1 | 3/2005 | Fairley et al. |
| 2005/0069217 A1 | 3/2005 | Mukherjee |
| 2005/0117796 A1 | 6/2005 | Matsui et al. |
| 2005/0132306 A1 | 6/2005 | Smith et al. |
| 2005/0141764 A1 | 6/2005 | Tohyama et al. |
| 2005/0166174 A1 | 7/2005 | Ye et al. |
| 2005/0184252 A1 | 8/2005 | Ogawa et al. |
| 2005/0190957 A1 | 9/2005 | Cai et al. |
| 2005/0198602 A1 | 9/2005 | Brankner et al. |
| 2006/0000964 A1 | 1/2006 | Ye et al. |
| 2006/0036979 A1 | 2/2006 | Zurbrick et al. |
| 2006/0038986 A1 | 2/2006 | Honda et al. |
| 2006/0048089 A1 | 3/2006 | Schwarzband |
| 2006/0051682 A1 | 3/2006 | Hess et al. |
| 2006/0062445 A1 | 3/2006 | Verma et al. |
| 2006/0066339 A1 | 3/2006 | Rajski et al. |
| 2006/0082763 A1 | 4/2006 | Teh et al. |
| 2006/0159333 A1 | 7/2006 | Ishikawa |
| 2006/0161452 A1 | 7/2006 | Hess |
| 2006/0193506 A1 | 8/2006 | Dorphan et al. |
| 2006/0193507 A1 | 8/2006 | Sali et al. |
| 2006/0236294 A1 | 10/2006 | Saidin et al. |
| 2006/0236297 A1 | 10/2006 | Melvin, III et al. |
| 2006/0239536 A1 | 10/2006 | Shibuya et al. |
| 2006/0265145 A1 | 11/2006 | Huet et al. |
| 2006/0266243 A1 | 11/2006 | Percin et al. |
| 2006/0269120 A1 | 11/2006 | Nehmadi et al. |
| 2006/0273242 A1 | 12/2006 | Hunsche et al. |
| 2006/0273266 A1 | 12/2006 | Preil et al. |
| 2006/0277520 A1 | 12/2006 | Gennari |
| 2006/0291714 A1 | 12/2006 | Wu et al. |
| 2006/0292463 A1 | 12/2006 | Best et al. |
| 2007/0002322 A1 | 1/2007 | Borodovsky et al. |
| 2007/0011628 A1 | 1/2007 | Ouali et al. |
| 2007/0013901 A1 | 1/2007 | Kim et al. |
| 2007/0019171 A1 | 1/2007 | Smith |
| 2007/0019856 A1 | 1/2007 | Furman et al. |
| 2007/0031745 A1 | 2/2007 | Ye et al. |
| 2007/0032896 A1 | 2/2007 | Ye et al. |
| 2007/0035322 A1 | 2/2007 | Kang et al. |
| 2007/0035712 A1 | 2/2007 | Gassner et al. |
| 2007/0035728 A1 | 2/2007 | Kekare et al. |
| 2007/0052963 A1 | 3/2007 | Orbon et al. |
| 2007/0064995 A1 | 3/2007 | Oaki et al. |
| 2007/0133860 A1 | 6/2007 | Lin et al. |
| 2007/0156379 A1 | 7/2007 | Kulkarni et al. |
| 2007/0230770 A1 | 10/2007 | Kulkarni et al. |
| 2007/0248257 A1 | 10/2007 | Bruce et al. |
| 2007/0280527 A1 | 12/2007 | Almogy et al. |
| 2007/0288219 A1 | 12/2007 | Zafar et al. |
| 2008/0013083 A1 | 1/2008 | Kirk et al. |
| 2008/0015802 A1 | 1/2008 | Urano et al. |
| 2008/0016481 A1 | 1/2008 | Matsuoka et al. |
| 2008/0018887 A1 | 1/2008 | Chen et al. |
| 2008/0049994 A1 | 2/2008 | Rognin et al. |
| 2008/0058977 A1 | 3/2008 | Honda |
| 2008/0072207 A1 | 3/2008 | Verma et al. |
| 2008/0081385 A1 | 4/2008 | Marella et al. |
| 2008/0163140 A1 | 7/2008 | Fouquet et al. |
| 2008/0167829 A1 | 7/2008 | Park et al. |
| 2008/0250384 A1 | 10/2008 | Duffy et al. |
| 2008/0295047 A1 | 11/2008 | Nehmadi et al. |
| 2008/0295048 A1 | 11/2008 | Nehmadi et al. |
| 2008/0304056 A1 | 12/2008 | Alles et al. |
| 2009/0024967 A1 | 1/2009 | Su et al. |
| 2009/0037134 A1 | 2/2009 | Kulkarni et al. |
| 2009/0041332 A1 | 2/2009 | Bhaskar et al. |
| 2009/0043527 A1 | 2/2009 | Park et al. |
| 2009/0055783 A1 | 2/2009 | Florence et al. |
| 2009/0067703 A1 | 3/2009 | Lin et al. |
| 2009/0080759 A1 | 3/2009 | Bhaskar et al. |
| 2009/0210183 A1 | 8/2009 | Rajski et al. |
| 2009/0257645 A1 | 10/2009 | Chen et al. |
| 2009/0284733 A1 | 11/2009 | Wallingford et al. |
| 2009/0290782 A1 | 11/2009 | Regensburger |
| 2009/0299681 A1 | 12/2009 | Chen et al. |
| 2009/0310864 A1* | 12/2009 | Takagi et al. ................ 382/190 |
| 2009/0323052 A1 | 12/2009 | Silberstein et al. |
| 2010/0142800 A1 | 6/2010 | Pak et al. |
| 2010/0146338 A1 | 6/2010 | Schalick et al. |
| 2010/0150429 A1 | 6/2010 | Jau et al. |
| 2010/0188657 A1 | 7/2010 | Chen et al. |
| 2010/0226562 A1 | 9/2010 | Wu et al. |
| 2011/0013825 A1 | 1/2011 | Shibuya et al. |
| 2011/0052040 A1 | 3/2011 | Kuan |
| 2011/0184662 A1 | 7/2011 | Badger et al. |
| 2011/0188733 A1* | 8/2011 | Bardos et al. ................ 382/149 |
| 2011/0251713 A1 | 10/2011 | Teshima et al. |
| 2011/0276935 A1 | 11/2011 | Fouquet et al. |
| 2011/0311126 A1 | 12/2011 | Sakai et al. |
| 2012/0308112 A1 | 12/2012 | Hu et al. |
| 2012/0319246 A1 | 12/2012 | Tan et al. |
| 2013/0009989 A1 | 1/2013 | Chen et al. |
| 2013/0027196 A1 | 1/2013 | Yankun et al. |

FOREIGN PATENT DOCUMENTS

| | | |
|---|---|---|
| CN | 1646896 | 7/2005 |
| CN | 101275920 | 10/2008 |
| EP | 0032197 | 7/1981 |
| EP | 0370322 | 5/1990 |
| EP | 1061358 | 12/2000 |
| EP | 1061571 | 12/2000 |
| EP | 1065567 | 1/2001 |
| EP | 1066925 | 1/2001 |
| EP | 1069609 | 1/2001 |
| EP | 1093017 | 4/2001 |
| EP | 1329771 | 7/2003 |
| EP | 1480034 | 11/2004 |
| EP | 1696270 | 8/2006 |
| JP | 7-159337 | 6/1995 |
| JP | 2002071575 | 3/2002 |
| JP | 2002-365235 | 12/2002 |
| JP | 2003-215060 | 7/2003 |
| JP | 2004-045066 | 2/2004 |
| JP | 2005-283326 | 10/2005 |
| JP | 2007-234798 | 9/2007 |
| JP | 2009-122046 | 6/2009 |
| JP | 2010-256242 | 11/2010 |
| JP | 2012-225768 | 11/2012 |
| KR | 10-2001-0007394 | 1/2001 |
| KR | 10-2001-0037026 | 5/2001 |
| KR | 10-2001-0101697 | 11/2001 |
| KR | 1020030055848 | 7/2003 |
| KR | 10-2005-0092053 | 9/2005 |
| KR | 10-2006-0075691 | 7/2006 |
| KR | 10-2006-0124514 | 12/2006 |
| KR | 10-0696276 | 3/2007 |
| KR | 10-2010-0061018 | 6/2010 |
| KR | 10-2012-0068128 | 6/2012 |
| WO | 9857358 | 12/1998 |
| WO | 9922310 | 5/1999 |

(56) References Cited

FOREIGN PATENT DOCUMENTS

| WO | 9925004 | 5/1999 |
|---|---|---|
| WO | 9959200 | 5/1999 |
| WO | 9938002 | 7/1999 |
| WO | 9941434 | 8/1999 |
| WO | 0003234 | 1/2000 |
| WO | 0036525 | 6/2000 |
| WO | 0055799 | 9/2000 |
| WO | 0068884 | 11/2000 |
| WO | 0070332 | 11/2000 |
| WO | 0109566 | 2/2001 |
| WO | 0140145 | 6/2001 |
| WO | 03104921 | 12/2003 |
| WO | 2004027684 | 4/2004 |
| WO | 2004/097903 | 11/2004 |
| WO | 2006/012388 | 2/2006 |
| WO | 2006063268 | 6/2006 |
| WO | 2009/152046 | 9/2009 |
| WO | 2010/093733 | 8/2010 |

OTHER PUBLICATIONS

Sahouria et al., "Full-chip Process Simulation for Silicon DRC," Mentor Graphics, Mar. 2000, 6 pages.
Schroder et al., Corona-Oxide-Semiconductor Device Characterization, 1998, Solid-State Electronics, vol. 42, No. 4, pp. 505-512.
Schroder, "Surface voltage and surface photovoltage: history, theory and applications," Measurement Science and Technology, vol. 12, 2001, pp. R16-31.
Schroder, Contactless Surface Charge Semiconductor Characterization, Apr. 2002, Materials Science and Engineering B, vol. 91-92, pp. 196-228.
Schurz et al., "Simulation Study of Reticle Enhancement Technology Applications for 157 nm Lithography," SPIE vol. 4562, 2002, pp. 902-913.
Svidenko et al. "Dynamic Defect-Limited Yield Prediction by Criticality Factor," ISSM Paper: YE-O-157, 2007.
Verkuil et al., "A Contactless Alternative to MOS Charge Measurements by Means of a Corona-Oxide-Semiconductor (COS) Technique,"Electrochem. Soc. Extended Abstracts, 1988, vol. 88-1, No. 169, pp. 261-262.
Verkuil, "Rapid Contactless Method for Measuring Fixed Oxide Charge Associated with Silicon Processing," IBM Technical Disclosure Bulletin, vol. 24, No. 6, 1981, pp. 3048-3053.
Volk et al. "Investigation of Reticle Defect Formation at DUV Lithography," 2002, BACUS Symposium on Photomask Technology.
Volk et al. "Investigation of Reticle Defect Formation at DUV Lithography," 2003, IEEE/SEMI Advanced Manufacturing Conference, pp. 29-35.
Volk et al., "Investigation of Smart Inspection of Critical Layer Reticles using Additional Designer Data to Determine Defect Significance," Proceedings of SPIE vol. 5256, 2003, pp. 489-499.
Weinberg, "Tunneling of Electrons from Si into Thermally Grown SiO2," Solid-State Electronics, 1977, vol. 20, pp. 11-18.
Weinzierl et al., "Non-Contact Corona-Based Process Control Measurements: Where We've Been, Where We're Headed," Electrochemical Society Proceedings, Oct. 1999, vol. 99-16, pp. 342-350.
Yan et al., "Printability of Pellicle Defects in DUV 0.5 um Lithography," SPIE vol. 1604, 1991, pp. 106-117.
U.S. Appl. No. 13/652,377, filed Oct. 15, 2012 by Wu et al.
Huang et al., "Using Design Based Binning to Improve Defect Excursion Control for 45nm Production," IEEE, International Symposium on Semiconductor Manufacturing, Oct. 2007, pp. 1-3.
Sato et al., "Defect Criticality Index (DCI): A new methodology to significantly improve DOI sampling rate in a 45nm production environment," Metrology, Inspection, and Process Control for Microlithography XXII, Proc. of SPIE vol. 6922, 692213 (2008), pp. 1-9.
Tang et al., "Analyzing Volume Diagnosis Results with Statistical Learning for Yield Improvement" 12th IEEE European Test Symposium, Freiburg 2007, IEEE European, May 20-24, 2007, pp. 145-150.

U.S. Appl. No. 60/681,095, filed May 13, 2005 by Nehmadi et al.
U.S. Appl. No. 60/684,360, filed May 24, 2005 by Nehmadi et al.
U.S. Appl. No. 10/778,752, filed Feb. 13, 2004 by Preil et al.
U.S. Appl. No. 10/793,599, filed Mar. 4, 2004 by Howard et al.
U.S. Appl. No. 11/139,151, filed Feb. 10, 2005 by Volk.
U.S. Appl. No. 11/154,310, filed Feb. 10, 2005 by Verma et al.
U.S. Appl. No. 12/394,752, filed Feb. 27, 2009 by Xiong et al.
U.S. Appl. No. 12/403,905, filed Mar. 13, 2009 by Xiong.
Allan et al., "Critical Area Extraction for Soft Fault Estimation," IEEE Transactions on Semiconductor Manufacturing, vol. 11, No. 1, Feb. 1998.
Barty et al., "Aerial Image Microscopes for the inspection of defects in EUV masks," Proceedings of SPIE, vol. 4889, 2002, pp. 1073-1084.
Budd et al., "A New Mask Evaluation Tool, the Microlithography Simulation Microscope Aerial Image Measurement System," SPIE vol. 2197, 1994, pp. 530-540.
Cai et al., "Enhanced Dispositioning of Reticle Defects Using the Virtual Stepper With Automated Defect Severity Scoring," Proceedings of the SPIE, vol. 4409, Jan. 2001, pp. 467-478.
Comizzoli, "Uses of Corona Discharges in the Semiconductor Industry," J. Electrochem. Soc., 1987, pp. 424-429.
Contactless Electrical Equivalent Oxide Thickness Measurement, IBM Technical Disclosure Bulletin, vol. 29, No. 10, 1987, pp. 4622-4623.
Contactless Photovoltage vs. Bias Method for Determining Flat-Band Voltage, IBM Technical Disclosure Bulletin, vol. 32, vol. 9A, 1990, pp. 14-17.
Cosway et al., "Manufacturing Implementation of Corona Oxide Silicon (COS) Systems for Diffusion Furnace Contamination Monitoring," 1997 IEEE/SEMI Advanced Semiconductor Manufacturing Conference, pp. 98-102.
Diebold et al., "Characterization and production metrology of thin transistor gate oxide films," Materials Science in Semiconductor Processing 2, 1999, pp. 103-147.
Dirksen et al., "Impact of high order aberrations on the performance of the aberration monitor," Proc. of SPIE vol. 4000, Mar. 2000, pp. 9-17.
Dirksen et al., "Novel aberration monitor for optical lithography," Proc. of SPIE vol. 3679, Jul. 1999, pp. 77-86.
Garcia et al., "New Die to Database Inspection Algorithm for Inspection of 90-nm Node Reticles," Proceedings of SPIE, vol. 5130, 2003, pp. 364-374.
Granik et al., "Sub-resolution process windows and yield estimation technique based on detailed full-chip CD simulation," Mentor Graphics, Sep. 2000, 5 pages.
Hess et al., "A Novel Approach: High Resolution Inspection with Wafer Plane Defect Detection," Proceedings of SPIE—International Society for Optical Engineering; Photomask and Next-Generation Lithography Mask Technology 2008, vol. 7028, 2008.
Huang et al., "Process Window Impact of Progressive Mask Defects, Its Inspection and Disposition Techniques (go/no-go criteria) Via a Lithographic Detector," Proceedings of SPIE—The International Society for Optical Engineering; 25th Annual Bacus Symposium on Photomask Technology 2005, vol. 5992, No. 1, 2005, p. 6.
Hung et al., Metrology Study of Sub 20 Angstrom oxynitride by Corona-Oxide-Silicon (COS) and Conventional C-V Approaches, 2002, Mat. Res. Soc. Symp. Proc., vol. 716, pp. 119-124.
International Search Report for PCT/US2003/021907 mailed Jun. 7, 2004.
International Search Report for PCT/US2004/040733 mailed Dec. 23, 2005.
International Search Report for PCT/US2006/061112 mailed Sep. 25, 2008.
International Search Report for PCT/US2006/061113 mailed Jul. 16, 2008.
International Search Report for PCT/US2008/050397 mailed Jul. 11, 2008.
International Search Report for PCT/US2008/062873 mailed Aug. 12, 2008.
International Search Report for PCT/US2008/062875 mailed Sep. 10, 2008.

(56) References Cited

OTHER PUBLICATIONS

International Search Report for PCT/US2008/063008 mailed Aug. 18, 2008.
International Search Report for PCT/US2008/066328 mailed Oct. 1, 2009.
International Search Report for PCT/US2008/070647 mailed Dec. 16, 2008.
International Search Report for PCT/US2008/072636 mailed Jan. 29, 2009.
International Search Report for PCT/US2008/073706 mailed Jan. 29, 2009.
Karklin et al., "Automatic Defect Severity Scoring for 193 nm Reticle Defect Inspection," Proceedings of SPIE—The International Society for Optical Engineering, 2001, vol. 4346, No. 2, pp. 898-906.
Lo et al., "Identifying Process Window Marginalities of Reticle Designs for 0.15/0.13 μm Technologies," Proceedings of SPIE vol. 5130, 2003, pp. 829-837.
Lorusso et al. "Advanced DFM Applns. Using design-based metrology on CDSEM," SPIE vol. 6152, Mar. 27, 2006.
Lu et al., "Application of Simulation Based Defect Printability Analysis for Mask Qualification Control," Proceedings of SPIE, vol. 5038, 2003, pp. 33-40.
Mack, "Lithographic Simulation: A Review," Proceedings of SPIE vol. 4440, 2001, pp. 59-72.
Martino et al., "Application of the Aerial Image Measurement System (AIMS(TM)) to the Analysis of Binary Mask Imaging and Resolution Enhancement Techniques," SPIE vol. 2197, 1994, pp. 573-584.
Miller, "A New Approach for Measuring Oxide Thickness," Semiconductor International, Jul. 1995, pp. 147-148.
Nagpal et al., "Wafer Plane Inspection for Advanced Reticle Defects," Proceedings of SPIE—The International Society for Optical Engineering; Photomask and Next-Generation Lithography Mask Technology. vol. 7028, 2008.
Numerical Recipes in C. The Art of Scientific Computing, 2nd Ed.,© Cambridge University Press 1988, 1992, p. 683.
O'Gorman et al., "Subpixel Registration Using a Concentric Ring Fiducial," Proceedings of the International Conference on Pattern Recognition, vol. ii, Jun. 16, 1990, pp. 249-253.
Otsu, "A Threshold Selection Method from Gray-Level Histograms," IEEE Transactions on Systems, Man, and Cybernetics, vol. SMC-9, No. 1, Jan. 1979, pp. 62-66.
Pang et al., "Simulation-based Defect Printability Analysis on Alternating Phase Shifting Masks for 193 nm Lithography," Proceedings of SPIE, vol. 4889, 2002, pp. 947-954.
Pettibone et al., "Wafer Printability Simulation Accuracy Based on UV Optical Inspection Images of Reticle Defects," Proceedings of SPIE—The International Society for Optical Engineering 1999 Society of Photo-Optical Instrumentation Engineers, vol. 3677, No. II, 1999, pp. 711-720.
International Search Report and Written Opinion for PCT/US2012/029676 mailed Oct. 29, 2012.
Guo et al., "License Plate Localization and Character Segmentation with Feedback Self-Learning and Hybrid Binarization Techniques," IEEE Transactions on Vehicular Technology, vol. 57, No. 3, May 2008, pp. 1417-1424.
Liu, "Robust Image Segmentation Using Local Median," Proceedings of the 3rd Canadian Conference on Computer and Robot Vision (CRV'06) 0-7695-2542-3/06, 2006 IEEE, 7 pages total.

\* cited by examiner

DESIGN-BASED INSPECTION USING REPEATING STRUCTURES

CROSS-REFERENCE TO RELATED APPLICATIONS

This application claims priority to U.S. Provisional Application No. 61/467,964 entitled "Design-based inspection using repeating structures," filed Mar. 25, 2011, which is incorporated by reference as if fully set forth herein.

BACKGROUND OF THE INVENTION

1. Field of the Invention

This invention generally relates to systems and methods for design-based inspection of wafers using repeating structures.

2. Description of the Related Art

The following description and examples are not admitted to be prior art by virtue of their inclusion in this section.

Inspection processes are used at various steps during a semiconductor manufacturing process to detect defects on wafers to promote higher yield in the manufacturing process and thus higher profits. Inspection has always been an important part of fabricating semiconductor devices. However, as the dimensions of semiconductor devices decrease, inspection becomes even more important to the successful manufacture of acceptable semiconductor devices because smaller defects can cause the devices to fail.

Inspection processes can be limited by various noise sources on the wafer. For example, one common inspection method is the die-to-die method that involves comparing output of an inspection system generated for corresponding positions in different dies formed on the wafer. In this manner, output generated for similar structures in multiple dies can be compared and the results of the comparison can be used to detect defects in those structures. However, due to process variations across the wafer, corresponding positions in different dies may have different characteristics such as film thickness and color variation that, while not actually defects, can be misidentified as defects in the die-to-die methods. The variations between dies can be accommodated by increasing the thresholds that are used to detect defects. However, increasing the threshold will obviously eliminate the detection of the smallest defects on the wafers.

Some inspection methods and/or systems detect defects by comparing output generated for multiple locations within a single die. There are generally two types of methods that utilize this concept in current inspection systems. However, their applicability is limited. For example, for array areas such as SRAM or DRAM areas of a die, by knowing the cell size within the array, a cell-to-cell inspection can be performed on wafer inspectors. There are also some existing systems that analyze the image stream during inspection and look for repeating structures by performing auto-correlation analysis and looking for periodic patterns. However, both of these methods are limited to layouts that have some periodicity (e.g., in the x direction) with a certain period.

Accordingly, it would be advantageous to develop inspection systems and/or methods that do not have one or more of the disadvantages described above.

SUMMARY OF THE INVENTION

The following description of various embodiments is not to be construed in any way as limiting the subject matter of the appended claims.

One embodiment relates to a computer-implemented method for inspecting a wafer. The method includes identifying multiple instances of structures in a design for a wafer. The structures have the same or substantially the same geometrical characteristics. Identifying the multiple instances is performed using design data for the design. The method also includes comparing output of an inspection system generated for two or more of the multiple instances formed on the wafer to each other. The two or more of the multiple instances are located within the same die on the wafer. In addition, the method includes detecting defects on the wafer based on results of the comparing. The identifying, comparing, and detecting steps are performed using a computer system.

Each of the steps of the method described above may be further performed as described herein. In addition, each of the steps of the method may be performed using any of the system(s) described herein. Furthermore, the method may include any other step(s) described herein.

Another embodiment relates to a non-transitory computer-readable medium storing program instructions executable on a computer system for performing a computer-implemented method for inspecting a wafer. The computer-implemented method executable by the program instructions includes the steps of the above-described computer-implemented method. The computer-readable medium may be further configured as described herein.

An additional embodiment relates to a system configured to inspect a wafer. The system includes an inspection subsystem configured to generate output for a wafer. The system also includes a computer subsystem configured for performing the steps of the computer-implemented method described above. The system may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Various embodiments for design-based inspection using repeating structures are described herein. One embodiment relates to a computer-implemented method for inspecting a wafer. The method includes identifying multiple instances of structures in a design for a wafer. The structures have the same or substantially the same geometrical characteristics. "Geometrical characteristics" as that term is used herein is intended to mean any characteristics of the structure that are related to the geometry of the structure. Therefore, "geometrical characteristics" may include such characteristics as width, height, side profile, shape of the structure, two-dimensional shape, three-dimensional shape, and the like. Therefore, structures that have the same geometrical characteristics would have the same width, height, side profile, shape of the structure, two-dimensional shape, three-dimensional shape, and the like. The term "substantially the same geometrical characteristics" references geometrical characteristics that are not different to such a degree that the differences themselves would be detected as defects in the methods described herein. In addition, the extent to which different geometrical characteristics can vary and still be considered substantially the same may vary depending upon the geometrical characteristic itself. For example, geometrical characteristics that are different by about 1% may be considered substantially the same for one characteristic while geometrical characteristics that are different by about 5% may be considered substantially the same for another characteristic.

A "structure" as that term is used herein is intended to mean a patterned structure that is formed on a wafer. In other words, the "structures" described herein are not simply films formed on a wafer. In addition, a "structure" as that term is used herein refers to a single continuous structure. In other words, a "structure" as that term is used herein does not refer to a collection of individual structures such as an array of lines, an array of contacts, or any other set of discrete structures. Instead, each of the lines, contacts, or discrete structures included in a set would each be a structure as that term is used herein.

Identifying the multiple instances is performed using design data for the design. For example, the embodiments described herein may use the design layout of a semiconductor layer to determine "similar" structures in relatively close proximity to one another in a die layout so that during inspection, these similar structures can be compared with each other and "outliers" marked as defects, the basic assumption being that such defect locations will be a substantially small fraction of all such similar structures. In one embodiment, identifying the multiple structures is not performed using output of an inspection system generated for a wafer. Instead, as described above, the repeating structures may be identified using the design data and in some cases only the design data. The design data may not include or be data or information acquired using a physical wafer. In other words, design data is not output generated by scanning a physical wafer or information or data generated based on such output. Since the repeating structures are identified in the embodiments described herein from analysis of design data, there is no image noise introduced into the algorithm. The embodiments described herein exploit the fact that some image computer systems can read in a large swath of data across a die and one can use the embodiments described herein to determine all locations of certain groups of geometries within that image buffer.

Several techniques may be used to find repeating structures in the design. For example, in one embodiment, identifying the multiple structures is performed without using periodicity of the structures. In another embodiment, the multiple instances do not occur in the design with any periodicity. For example, the embodiments described herein may look for similar patterns even if they are not periodic.

In some embodiments, identifying the multiple structures is not performed based on cell size of the design. In this manner, the embodiments described herein may be independent of cell size, which is different than some methods used for array inspection. For example, in some currently used methods for array areas such as SRAM or DRAM areas of a die, by knowing the cell size within the array, a cell-to-cell inspection is performed on wafer inspectors. However, these methods are limited to layouts that have some periodicity (e.g., in the x or scanning direction) with a certain period. In contrast, the embodiments described herein can utilize the repeating nature of certain structures within the design regardless of the cell size, periodicity, frequency, and any other cell characteristics. Therefore, the embodiments described herein may be much more flexible in the types of structures that can be used as repeating structures, the algorithms that are used to detect defects in those repeating structures, and the way defects in different repeating structures are classified.

In some embodiments, each of the multiple instances includes only one structure in the design. For example, each repeating structure itself may be identified and used as a single instance of the structure. In this manner, for defect detection purposes, the output for one repeating structure may be used for comparison to output for at least one other of the same or substantially the same repeating structure.

In another embodiment, each of the multiple instances includes multiple structures in the design. For example, the method may find groups of geometries that occur in various places in the layout. The groups of geometries do not have to occur with any fixed periodicity. Such groups of geometries may be identified as described further herein.

Figure 1:
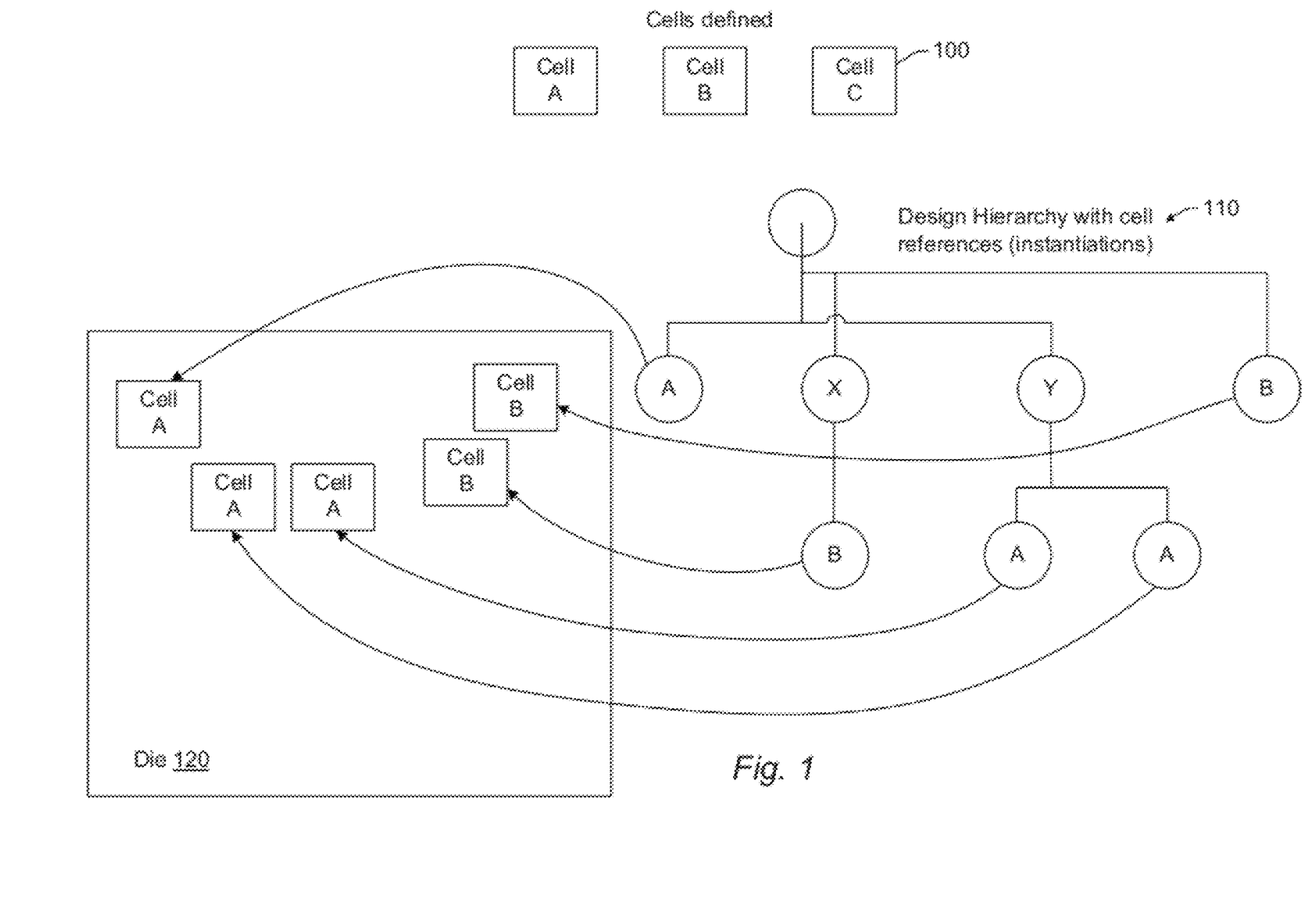
FIG. 1 is a schematic diagram illustrating one embodiment of cell instantiation analysis.

In one embodiment, identifying the multiple instances includes identifying multiple instances of the same design cell in the design using a design layout hierarchy for the design. In this manner, identifying the multiple instances may include cell instantiation analysis. For example, in this method, the design layout hierarchy is examined and instances of the same design "cell" in the layout are identified. In particular, as shown in FIG. 1, the method may include defining cells 100 (e.g., Cell A, Cell B, Cell C, etc) in the design. The method may also include using the design hierarchy with cell references (instantiations) 110 to search in design data for die 120 for the various cells (e.g., Cell A, Cell B, etc.). These areas can be assumed to look similar on the scanned die.

In some embodiments, identifying the multiple instances includes searching the design data for any instances of a known pattern of interest by performing a polygon match of the structures that make up the known pattern of interest and the structures in the design data. For example, if a pattern of interest (POI) is known a priori, the design can be searched for all locations of the same pattern by performing a polygon match of the figures that make up the POI.

In an additional embodiment, identifying the multiple instances includes performing Fourier analysis of the design data. For example, Fourier analysis of the design may be performed either by rendering it or by analyzing the polygonal representation and looking for periodicities in the x (comparing) direction.

Figure 2:
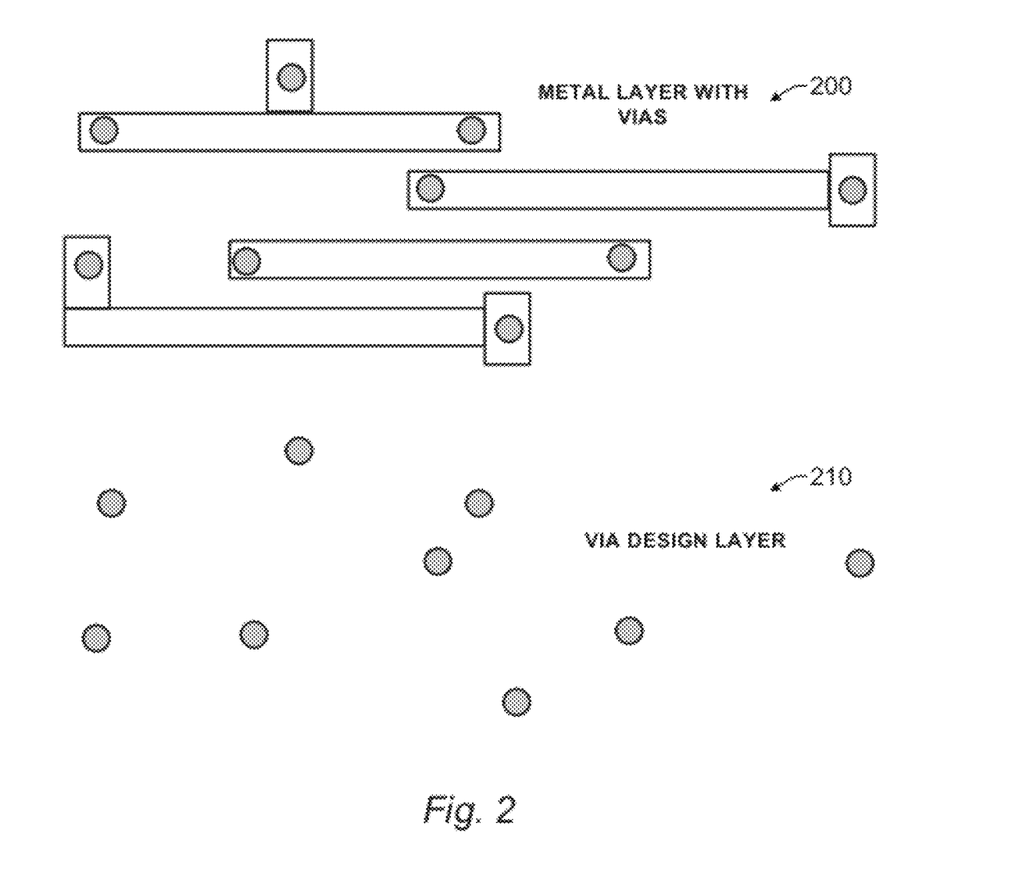
FIG. 2 is a schematic diagram illustrating one example of similar structures that are self-evident from design "layer" intent itself.

In one embodiment, identifying the multiple instances is performed using design layer intent for the design data. For example, certain structures that are similar may be self-evident from the design "layer" intent itself. In one such example, a via/contact layer is simply a set of identical small structures and other than the center location and dimensions of each via/contact, no further processing is required to identify "similarity." In one particular example, as shown in FIG. 2, one layer may be the metal layer with vias 200, and the corresponding via design layer 210 may be used to identify the center location and dimensions of each via/contact.

In a further embodiment, identifying the multiple instances includes analyzing a design layout for the design data at a polygonal level to identify the multiple instances of the structures. In this manner, the design layout can be analyzed at the polygonal level to find similar collections of neighboring geometries that repeat in several places in the design. These can be marked as belonging to one "care area group" and can be compared with each other within a die instead of in a die-to-die comparison. One example of an algorithm that can be used to find repeating structures is described in Gu et al., "Lossless compression algorithms for hierarchical IC layouts," IEEE Transactions on Semiconductor Manufacturing, Vol. 21, No. 2, May 2008, which is incorporated by reference as if fully set forth herein. Although the algorithm described in this paper is used for the purposes of compressing the design representation, this algorithm, or a similar one, may be used to identify repeating structures for comparison purposes during inspection.

Figure 3:
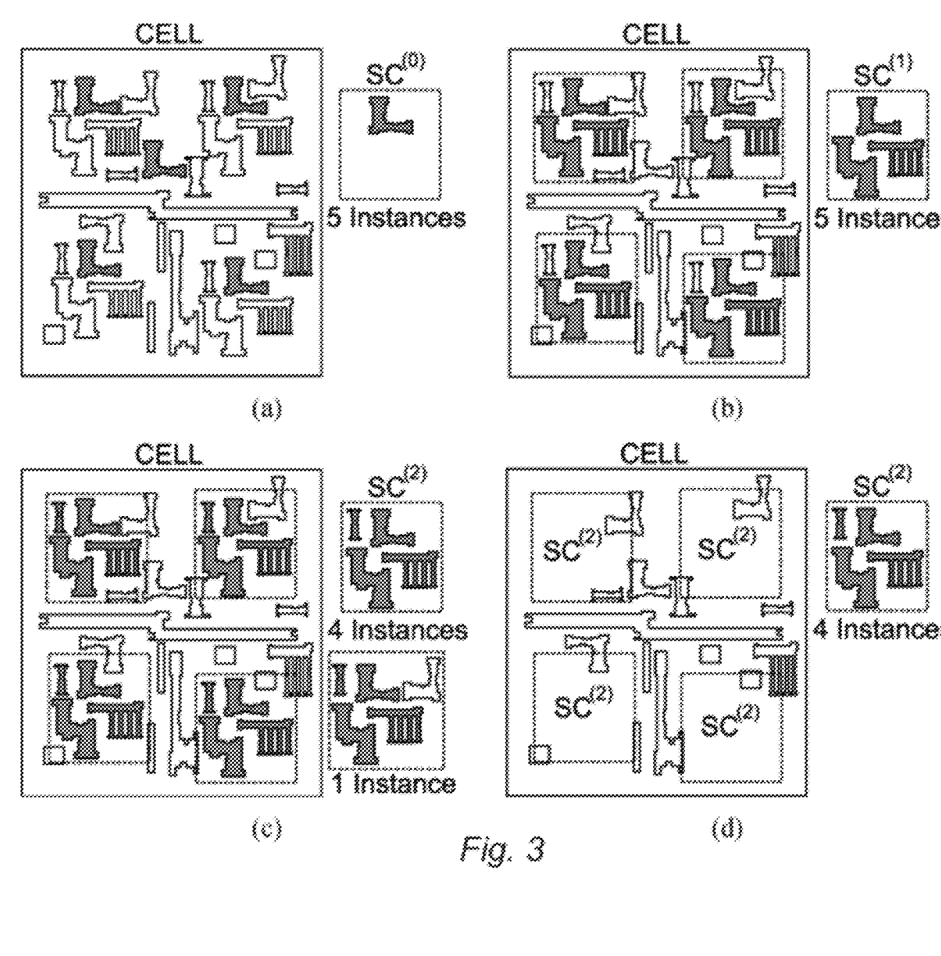
FIG. 3 is a schematic diagram illustrating one embodiment of how an iterative algorithm can rank and detect repeating geometries.

In some embodiments, identifying the multiple instances is performed by identifying a first structure in the design data that can be included in the multiple instances and then iteratively searching the design data for other structures that can also be included in the multiple instances with the first structure. For example, FIG. 3 is taken from the above-referenced paper and shows how an iterative algorithm ranks and detects repeating geometries. In particular, FIG. 3 shows an intracell subcell detection example in which (a) shows the 0th iteration; (b) shows the first iteration; (c) shows the second iteration; and (d) shows the final result. In this example, as shown in the 0th iteration, the algorithm may search the cell for a single selected structure and find 5 instances of the single structure within the cell. Each of the 5 instances has the same geometrical characteristics (e.g., shape, dimensions, and orientation) in the cell. The algorithm may then define the subcell as SC(0) shown in FIG. 3, 5 instances of which were found, each containing one instance of the structure and some space around the structure.

In the next iteration, the algorithm searches the cell for instances of other structures that are near more than one instance of the first structure included in SC(0) (i.e., other structures having the same geometrical characteristics as each other and that are repeating with the first structure). For example, as shown in FIG. 3, the algorithm may search the cell again and identify two other structures that are located near more than one instance of the first "L" shaped structure. Each of the two other identified structures have the same geometrical characteristics as each other (e.g., the same shape as each other and the same spatial relationship with respect to the first structure). The algorithm may then define the subcell SC(1) shown in FIG. 3, 4 instances of which were found, each containing one instance of 3 different structures and some space around the structures.

The algorithm may perform any additional number of iterations. For example, as shown in FIG. 3, the algorithm may search the cell again and identify one other structure that is located near more than one instance of the first "L" shaped structure. Each instance of this other identified structure has the same geometrical characteristics as each other (e.g., the same shape and the same spatial relationship with respect to the first structure). The algorithm may then define the subcell as SC(2) shown in FIG. 3, 4 instances of which were found, each containing one instance of 4 different structures and some space around the structures. As also shown in this example, the algorithm may search the cell in the space in and around one of the subcells and identify another structure that is near the first structure. However, upon searching the other subcells the corresponding areas in which that additional structure was found in the first instance, that other structure was not found in the other subcells. In this manner, there is only one instance of the structure and it is not repeating. Therefore, this other structure is not included in the subcell results (i.e., SC(2)), and this subcell is not included in the results (e.g., it is not another repeating subcell). Therefore, as shown in the final result, the subcell SC(2) defines each of the multiple (4) instances of the repeating structures.

In another embodiment, the multiple instances include at least three instances of the structures. For example, different inspection methods may require a different minimum number of repeats of a structure. In one such example, in a die-to-die type method, defect arbitration is performed by comparing three adjacent die locations by doing two die-pair comparisons, where each comparison is preceded by an alignment/interpolation step to align the pixels to a sub-pixel (typically less than 0.05 pixels) accuracy. The method performs interpolations of a sub-frame (256 pixels×256 pixels) at a time in bright field (BF) tools, the alignment offset (delta x, delta y) being provided by a real time alignment (RTA) system. One could therefore argue that the minimum number of repeats of a structure required to arbitrate a defect location is three. Therefore, to perform a similar defect arbitration using the multiple instances described herein, at least three instances of the structures would be needed. However, having many more occurrences of the structure within an image frame allows one to use statistics to flag outliers in a more robust manner. For example, in one embodiment, the multiple instances include all instances of the structures in the design data.

The method also includes comparing output of an inspection system generated for two or more of the multiple instances formed on the wafer to each other. The two or more of the multiple instances are located within the same die on the wafer. In this manner, the embodiments described herein bypass the die-to-die method of random mode defect detection and in some way mimic the array-mode detection algorithm. The advantage of the embodiments described herein over die-to-die random mode is that the die-to-die noise sources are removed and one can potentially lower the detection threshold thereby enabling more sensitive inspection.

In one embodiment, prior to the comparing step, the method includes interpolating the multiple instances of the structures to a common pixel grid. For example, all occurrences of the structure may be interpolated to a common pixel grid before performing the comparisons (differencing their gray level values from corresponding pixel locations). Clearly, interpolation errors will introduce a noise source. However, for a properly sampled image, this noise source may be much less than the die-to-die noise, particularly in electron beam based inspection systems.

In a further embodiment, during inspection and prior to the comparing step, the method includes aligning the output generated for the two or more of the multiple instances in corresponding pixel streams of the output. For example, the embodiments described herein assume one can accurately align the similar areas (detected from analyzing the design) with the corresponding pixel stream during inspection.

The method further includes detecting defects on the wafer based on results of the comparing. For example, detecting the defects may include applying some threshold to the results of the comparing step, and any output determined to be above the threshold may be identified as corresponding to a defect. The threshold may include any suitable threshold known in the art.

The identifying, comparing, and detecting steps are performed using a computer system. The computer system may be further configured as described herein.

The embodiments described herein have a number of advantages over other inspection systems and methods. For example, by comparing two structures within the same die, rather than die-to-die comparisons as is done for inspecting logic areas, the die-to-die noise such as changes in film thickness, focus, etc. are eliminated. In addition, the embodiments described herein may find all repeats of a certain set of geometries within a die, while the current methods look for periodicity (in the scanning (and comparison) direction). Thus, the embodiments described herein are more general than the current methods. Furthermore, the embodiments described herein use design data rather than trying to infer from the wafer image where the repeating structures are located. Using the design has the advantage that it is the ideal representation (intent) of what the wafer image should look like, uncorrupted by image noise sources in the image acquisition system.

All of the methods described herein may include storing results of one or more steps of the methods in a storage medium. The results may include any of the results described herein and may be stored in any manner known in the art. The storage medium may include any suitable computer-readable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time.

Figure 4:
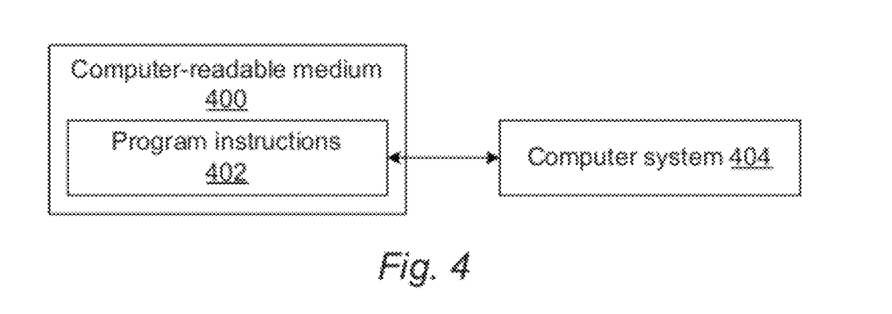
FIG. 4 is a block diagram illustrating one embodiment of a non-transitory computer-readable medium.

FIG. 4 illustrates one embodiment of non-transitory computer-readable medium 400 storing program instructions 402 executable on computer system 404 for performing a computer-implemented method for inspecting a wafer. The method for which program instructions 402 are executable on computer system 404 may include any step(s) of any method (s) described herein. In some embodiments, computer system 404 may be a computer system of an inspection system as described further herein. In some alternative embodiments, the computer system may be connected to the inspection system by a network. However, in other embodiments, computer system 404 may not be coupled to or included in an inspection system. In some such embodiments, computer system 404 may be configured as a stand alone computer system. Computer-readable medium 400, program instructions 402, and computer system 404 may be further configured as described herein.

Program instructions 402 implementing methods such as those described herein may be stored on computer-readable medium 400. The computer-readable medium may be a storage medium such as a read-only memory, a random access memory, a magnetic or optical disk, a magnetic tape, or other non-transitory computer-readable medium.

The program instructions may be implemented in any of various ways, including procedure-based techniques, component-based techniques, and/or object-oriented techniques, among others. For example, the program instructions may be implemented using ActiveX controls, C++ objects, C#, JavaBeans, Microsoft Foundation Classes ("MFC"), or other technologies or methodologies, as desired.

The computer system may include any suitable computer system known in the art. For example, computer system 404 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

Figure 5:
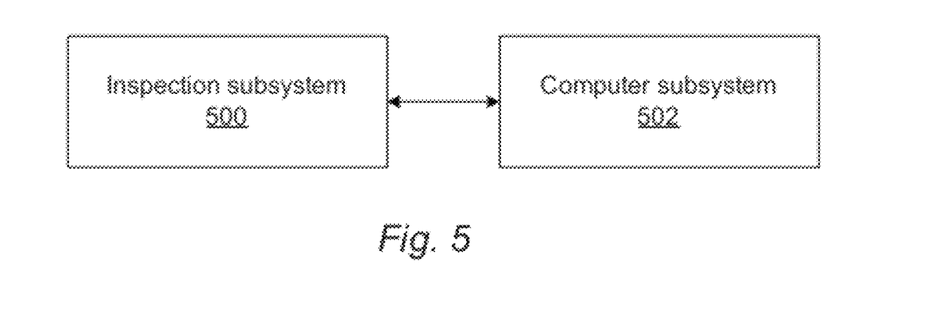
FIG. 5 is a block diagram illustrating one embodiment of a system.

Another embodiment relates to a system configured to inspect a wafer. For example, as shown in FIG. 5, the system includes inspection subsystem 500 configured to generate output for a wafer. The inspection subsystem may include an inspection subsystem of any commercially available wafer inspection system. The inspection subsystem may also be configured for any suitable inspection methods such as bright field inspection, dark field inspection, optical (light-based) inspection, electron beam based inspection, etc., or some combination thereof. The system also includes computer subsystem 502 configured for performing the steps of the methods described above. Computer subsystem 502 may be further configured as described above with respect to computer system 404. The computer subsystem and the system may be further configured as described herein.

Further modifications and alternative embodiments of various aspects of the invention may be apparent to those skilled in the art in view of this description. For example, systems and methods for design-based inspection using repeating structures are provided. Accordingly, this description is to be construed as illustrative only and is for the purpose of teaching those skilled in the art the general manner of carrying out the it) invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for inspecting a wafer, comprising:
    identifying multiple instances of structures in a design for a wafer, wherein the structures have the same or substantially the same geometrical characteristics, wherein each of the structures included in the multiple instances comprises a single continuous structure, and wherein said identifying is performed using design data for the design;
    comparing output of an inspection system generated for two or more of the multiple instances of the single continuous structures formed on the wafer to each other, wherein the two or more of the multiple instances are located within the same die on the wafer, and wherein the output that is compared for the two or more of the multiple instances comprises all of the output generated for the single continuous structures included in the two or more of the multiple instances; and detecting defects on the wafer based on results of said comparing, wherein said identifying, said comparing, and said detecting are performed using a computer system.

2. The method of claim 1, wherein said identifying is further performed without using periodicity of the structures.

3. The method of claim 1, wherein said identifying is not performed using output of an inspection system generated for a wafer.

4. The method of claim 1, wherein said identifying is not performed based on cell size of the design.

5. The method of claim 1, wherein the multiple instances do not occur in the design with any periodicity.

6. The method of claim 1, wherein each of the multiple instances comprise only one structure in the design.

7. The method of claim 1, wherein each of the multiple instances comprise multiple structures in the design.

8. The method of claim 1, wherein said identifying comprises identifying multiple instances of the same design cell in the design using a design layout hierarchy for the design.

9. The method of claim 1, wherein said identifying comprises searching the design data for any instances of a known pattern of interest by performing a polygon match of the structures that make up the known pattern of interest and the structures in the design data.

10. The method of claim 1, wherein said identifying comprises performing Fourier analysis of the design data.

11. The method of claim 1, wherein said identifying is further performed using design layer intent for the design data.

12. The method of claim 1, wherein said identifying comprises analyzing a design layout for the design data at a polygonal level to identify the multiple instances of the structures.

13. The method of claim 1, wherein said identifying is performed by identifying a first structure in the design data that can be included in the multiple instances and then iteratively searching the design data for other structures that can also be included in the multiple instances with the first structure.

14. The method of claim 1, wherein the multiple instances comprise at least three instances of the structures.

15. The method of claim 1, wherein the multiple instances comprise all instances of the structures in the design data.

16. The method of claim 1, further comprising prior to said comparing, interpolating the multiple instances of the structures to a common pixel grid.

17. The method of claim 1, further comprising during inspection and prior to said comparing, aligning the output generated for the two or more of the multiple instances in corresponding pixel streams of the output.

18. A non-transitory computer-readable medium storing program instructions executable on a computer system for performing a computer-implemented method for inspecting a wafer, wherein the computer-implemented method comprises:

identifying multiple instances of structures in a design for a wafer, wherein the structures have the same or substantially the same geometrical characteristics, wherein each of the structures included in the multiple instances comprises a single continuous structure, and wherein said identifying is performed using design data for the design;

comparing output of an inspection system generated for two or more of the multiple instances of the single continuous structures formed on the wafer to each other, wherein the two or more of the multiple instances are located within the same die on the wafer, and wherein the output that is compared for the two or more of the multiple instances comprises all of the output generated for the single continuous structures included in the two or more of the multiple instances; and detecting defects on the wafer based on results of said comparing.

19. A system configured to inspect a wafer, comprising:

an inspection subsystem configured to generate output for a wafer; and a computer subsystem configured for:

identifying multiple instances of structures in a design for the wafer, wherein the structures have the same or substantially the same geometrical characteristics, wherein each of the structures included in the multiple instances comprises a single continuous structure, and wherein said identifying is performed using design data for the design;

comparing output of the inspection subsystem generated for two or more of the multiple instances of the single continuous structures formed on the wafer to each other, wherein the two or more of the multiple instances are located within the same die on the wafer, and wherein the output that is compared for the two or more of the multiple instances comprises all of the output generated for the single continuous structures included in the two or more of the multiple instances; and detecting defects on the wafer based on results of said comparing.

20. The system of claim 19, wherein said identifying is further performed without using periodicity of the structures.

21. The system of claim 19, wherein said identifying is not performed using output of the inspection subsystem generated for a wafer.

22. The system of claim 19, wherein said identifying is not performed based on cell size of the design.

23. The system of claim 19, wherein the multiple instances do not occur in the design with any periodicity.

24. The system of claim 19, wherein each of the multiple instances comprise only one structure in the design.

25. The system of claim 19, wherein each of the multiple instances comprise multiple structures in the design.

26. The system of claim 19, wherein said identifying comprises identifying multiple instances of the same design cell in the design using a design layout hierarchy for the design.

27. The system of claim 19, wherein said identifying comprises searching the design data for any instances of a known pattern of interest by performing a polygon match of the structures that make up the known pattern of interest and the structures in the design data.

28. The system of claim 19, wherein said identifying comprises performing Fourier analysis of the design data.

29. The system of claim 19, wherein said identifying is further performed using design layer intent for the design data.

30. The system of claim 19, wherein said identifying comprises analyzing a design layout for the design data at a polygonal level to identify the multiple instances of the structures.

31. The system of claim 19, wherein said identifying is performed by identifying a first structure in the design data that can be included in the multiple instances and then iteratively searching the design data fir other structures that can also be included in the multiple instances with the first structure.

32. The system of claim 19, wherein the multiple instances comprise at least three instances of the structures.

33. The system of claim 19, wherein the multiple instances comprise all instances of the structures in the design data.

34. The system of claim 19, wherein the computer subsystem is further configured for, prior to said comparing, interpolating the multiple instances of the structures to a common pixel grid.

35. The system of claim 19, wherein the computer subsystem is further configured for, during inspection and prior to said comparing, aligning the output generated for the two or more of the multiple instances in corresponding pixel streams of the output.

* * * * *